(12) United States Patent
Rupp et al.

(10) Patent No.: US 7,309,706 B2
(45) Date of Patent: Dec. 18, 2007

(54) METHOD FOR THE TREATMENT OF DISEASES REQUIRING INHIBITION OR A REDUCTION IN THE ACTIVITY OF PH VALUE-REGULATING BICARBONATE TRANSPORTER PROTEINS

(75) Inventors: Heinz Rupp, Gomaringen (DE); Bernd Eisele, Laatzen (DE); Dieter Ziegler, Hemmingen (DE); Bodo Jaeger, Hannover (DE); Bernhard Maisch, Marburg (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 11/013,326

(22) Filed: Dec. 17, 2004

(65) Prior Publication Data

US 2005/0165080 A1 Jul. 28, 2005

Related U.S. Application Data

(63) Continuation of application No. PCT/EP03/06319, filed on Jun. 16, 2003.

(30) Foreign Application Priority Data

Jun. 19, 2002 (EP) ................... 02013387

(51) Int. Cl.
*A61K 31/513* (2006.01)
*A61K 31/498* (2006.01)
(52) U.S. Cl. ....................... 514/269; 514/401
(58) Field of Classification Search ........... 514/269, 514/256, 377, 401, 426, 412, 255
See application file for complete search history.

(56) References Cited

U.S. PATENT DOCUMENTS

| | | | |
|---|---|---|---|
| 3,988,464 A | 10/1976 | Malen et al. | |
| 4,102,890 A | 7/1978 | Malen et al. | |
| 4,323,570 A | 4/1982 | Stenzel et al. | |
| 4,952,410 A * | 8/1990 | Armah et al. | 424/465 |
| 5,492,912 A | 2/1996 | Godfroid et al. | |
| 5,500,426 A | 3/1996 | Godfroid et al. | |
| 5,686,477 A | 11/1997 | Jarry et al. | |
| 5,703,118 A | 12/1997 | Durand et al. | |
| 5,712,283 A * | 1/1998 | Kaan et al. | 514/269 |
| 5,732,717 A * | 3/1998 | Watanabe et al. | 128/898 |
| 5,741,796 A | 4/1998 | Hartman et al. | |
| 5,804,587 A * | 9/1998 | Cupps et al. | 514/314 |
| 5,925,665 A | 7/1999 | Payard et al. | |
| 6,005,117 A | 12/1999 | Wehner et al. | |
| 6,054,461 A * | 4/2000 | Fairbanks et al. | 514/269 |
| 6,117,879 A * | 9/2000 | Fairbanks et al. | 514/269 |
| 6,204,271 B1 * | 3/2001 | Fairbanks et al. | 514/269 |
| 6,300,336 B1 | 10/2001 | Eeckhout et al. | |
| 6,300,366 B1 | 10/2001 | Bousquet et al. | |
| 6,475,752 B1 * | 11/2002 | Lal et al. | 435/69.1 |
| 6,777,394 B1 * | 8/2004 | Prell | 514/43 |
| 2001/0053777 A1 * | 12/2001 | Brecht | 514/221 |
| 2002/0161191 A1 * | 10/2002 | Feder et al. | 530/350 |
| 2003/0181354 A1 * | 9/2003 | Abdulrazik | 514/1 |

FOREIGN PATENT DOCUMENTS

| | | |
|---|---|---|
| DE | 2 362 754 | 7/1974 |
| DE | 28 49 537 A1 | 5/1980 |
| EP | 0 638 568 A1 | 7/1974 |
| EP | 0 710 658 A1 | 5/1996 |
| EP | 0 638 568 B1 | 10/1996 |
| EP | 0 740 936 A2 | 11/1996 |
| EP | 0 820 988 A2 | 1/1998 |
| EP | 0 846 688 A1 | 6/1998 |
| EP | 1 038 526 A1 | 9/2000 |
| EP | 1 101 756 A1 | 5/2001 |
| WO | WO 00/02878 | 1/2000 |
| WO | WO 01/41764 A1 | 6/2001 |

OTHER PUBLICATIONS ("Osteoporosis: No Cure, But Treatment Offer Relief", www.ucihealth.com, 2006.*
"Boning Up on Osteoporosis", www.fda.gov, 2004.*
"Rheumatoid Arthritis treatments", Matsumoto et al., www.hopkins-arthritis.com, 2006.*
"Medical Treatment Decisions for People with Paget's Disease of Bone", www.niams.nih.gov, 2005.*
I1 imidzoline receptor agonists, Ian Musgrave, ian.Musgrave at med.monash.edu.au, Aug. 1, 1996.*
("Pharmacological and molecular discrimination of brain I2-imidazoline receptor subtypes", Olmos et al., Naunym Schmiedebergs Arch Pharmacol., 1996, abstract, 354 (6):709-16.*
Avkiran M, Marber MS. Na(+)/H(+) exchange inhibitors for card ioprotective therapy: progress, problems and prospects. J Am Coll Cardiol Mar. 6, 2002;39(5):747-53.
Bock et al. (1999) Analysis of the receptor involved in the central hypotensive effect of rilmenidine and moxonidine. Naunyn Schmiedebergs Arch Pharmacol. 359:262-71.

(Continued)

*Primary Examiner*—Brian Kwon
(74) *Attorney, Agent, or Firm*—Crowell & Moring LLP (57) ABSTRACT

The use of selective imidazoline receptor agonists, such as moxonidine, rilmenidine, LNP-509, S-23515, PMS-812, PMS-847 and BU-98008, and their physiologically compatible acid addition salts in pharmaceutical preparations for the treatment and/or inhibition of functional disorders and/or diseases in larger mammals or humans which require inhibition or reduction of the activity of proteins which regulate the intracellular pH value and which belong to the superfamily of bicarbonate transporters, in particular the treatment or inhibition of clinical conditions of bones which are caused by an undesirable amount of bone resorption, such as osteoporosis; of diseases of the gastrointestinal tract, such as gastric ulcers; and of neuronal and/or neuropsychiatric diseases associated with a pathologically altered (especially increased) neuronal activity, such as depression, Alzheimer's disease, eating disorders and schizophrenia.

6 Claims, 1 Drawing Sheet

OTHER PUBLICATIONS

Bonnet et al. (2000) Alteration of intracellular pH and activity of CA3-pyramidal cells in guinea pig hippocampal slices by inhibition of transmembrane acid extrusion. Brain Res. 872:116-24.

Boron & De Weer (1976) Intracellular pH transients in squid giant axons caused by CO2, NH3, and metabolic inhibitors. J Gen Physiol. 67:91-112.

Boron (2001) Sodium-coupled bicarbonate transporters. JOP 24(Suppl):176-81.

Bosman GJ, Renkawek K, Van Workum FP, Bartholomeus IG, Marini S, De Grip WJ. Neuronal anion exchange proteins in Alzheimer's disease pathology. J Neural Transm Suppl 1998;54:248-57.

Brilla et al. (1994) Collagen metabolism in cultured adult rat cardiac fibroblasts: response to angiotensin II and aldosterone. J. Mol. Cell Cardiol. 26:809-820.

Canzoniero et al. (1996) Recovery from NMDA-induced intracellular acidification is delayed and dependent on extracellular bicarbonate. Am J Physiol. 270:C593-9.

Chambers et al. (1985) The effect of calcium-regulating hormones and prostaglandins on bone resorption by osteoclasts disaggregated from neonatal rabbit bones. Endocrinology 116:234-9.

Emsberger (2000) Pharmacology of moxonidine: an I1-imidazoline receptor agonist. J Cardiovasc Pharmacol. 35:S27-41.

Gary B. Glavin & Donald D. Smyth, Effects of the selective I imidazoline receptor agonist, moxonidine, on gastric secretion and gastric mucosal injury in rats, British Journal of Pharmacology (1995)114, 751-754.

Hall et al. (1989) Optimal bone resorption by isolated rat osteoclasts requires chloride/bicarbonate exchange, Calcif Tissue Int. 45:378-80.

Hieble & Ruffolo (1995) Possible structural and functional relationships between imidazoline receptors and alpha 2-adrenoceptors. Ann N Y Acad Sci. 763:8-21.

Lagadic-Gossmann, D.; Prigent, K. Le: Baut, G. Le; Caignard, D. H. Renard, P. Scalbert, E.; Feuvray, D. (1996) Effects of S20787 on pHi-Regulating Mechanisms in Isolated Rat Ventricular Myocytes vol. 28(4),pp. 547-552 Lippincott-Raven Publishers.

Le Bihan et al. (1999) Design and synthesis of imidazoline derivatives active on glucose homeostasis in a rat model of type II diabetes. 2. Syntheses and biological activities of 1,4dialkyl-,1,4-dibenzyl, and 1-benzyl-4-alkyl-2-(4',5'-dihydro-1'H-imidazol-2'-yl)piperazines and isosteric analogues of imidazoline. J Med Chem. 42:1587-603.

Muallem et al. (1988) Activation of the Na+/H+ and Cl-/HCO3- exchange by stimulation of acid secretion in the parietal cell. J Biol Chem. 263:14703-11.

D.J. Nutt, N. French, S. Handly, A. Hudson, S. Husbands, H. Jackson, S. Jordan, M.D. Lalies, J. Lewis, L. Lione, N. Mallard and J. Pratt. Functional Studies of Specific Imidazoline-2 Receptor Ligands, Annals New York Academy of Sciences, 125-39.

Poisson D., Montaron, Garrigue, MUh & Sannajust Neuroprotective Efects Of Rilmendine On Neuronal And Glial Cell Injuries Induced By Hypoxia, pl53.

Puceat (1999) PHi regulatory ion transporters: an update on stricture, regulation and cell function, Review, Cell Mol Life Sci, 55(10), 1216-25.

D.J. Reis, MD, S. Regunathan, Phd, E.V. Golanov, MD, PhD and D.L. Feinstein, PhD, Protection of Focal Ischemic Infarction by Rilmenidine in the Animal: Evidence That Interactions with Central Imidazoline Receptors May Be Neuroprotective, The American Journal of Cardiology, 74 (1994) 25A.

Romero et al. (2000) Cloning and characterization of a NA+-driven anion exchanger (NDAE1). A new bicarbonate transporter. J Biol Chem 275:24552-9.

Rondu et al. (1997) Design and synthesis of imidazoline derivatives active on glucose homeostasis in a rat model of type II diabetes. 1. Synthesis and biological activities of N-benzylN'-(arylalkyl)-2-(4',5'-dihydro-1'H-imidazol-2'-yl)piperazines. J Med Chem. 40:3793-803.

Eberhard Schlatter, Jeva Ankorina-Stark, Sabine Haxelmans and Helge Hohage Moxonidine inhibits Na+/H+ exchange in proximal tubule cells and cortical collecting duct Kidney International, vol. 52 (1997), pp. 454-459.

Schann et al. (2001) Synthesis and biological evaluation of pyrrolinic isosteres of rilmenidine. Discovery of cis-/trans-dicyclopropylmethyl-(4,5-dimethyl-4,5-dihydro-3H-pyrrol-2-yl)amine (LNP 509), an I1 imidazoline receptor selective ligand with hypotensive activity. J Med Chem. 44:1588-93.

Takagi & Okabe (1968) The effects of drugs on the production and recovery processes of the stress ulcer. Jpn J Pharmacol. 18:9-18.

Takahashi & Copenhagen (1996) Modulation of neuronal function by intracellular pH. Neurosci Res. 24:109-16.

Teti et al. (1989) Cytoplasmic pH regulation and chloride/bicarbonate exchange in avian osteoclasts. J Clin Invest. 83:227-33.

Trapp et al. (1996) Acidosis of rat dorsal vagal neurons in situ during spontaneous and evoked activity. J Physiol. 496:695-710.

Urcelay E, Ibarreta D, Parrilla R, Ayuso MS, Martin-Requero A. Enhanced proliferation of lymphoblasts from patients with Alzheimer dementia associated with calmodulin-dependent activation of the na+/H+ exchanger; Neurobiol Dis 2001;8:289-98.

Imidazoline Receptors—IUPHAR Satellite Symposium Bonn, Germany Head GA, IDDB Meeting Report 1998, Jul. 22-24.

* cited by examiner

Fig. 1

METHOD FOR THE TREATMENT OF DISEASES REQUIRING INHIBITION OR A REDUCTION IN THE ACTIVITY OF PH VALUE-REGULATING BICARBONATE TRANSPORTER PROTEINS

CROSS REFERENCE TO RELATED APPLICATIONS

This application is a continuation of international patent application no. PCT/EP03/006319, filed Jun. 16, 2003, designating the United States of America, and published in German as WO 2004/000312 on Dec. 31, 2003, the entire disclosure of which is incorporated herein by reference. Priority is claimed based on European patent application no. EP 02013387.2, filed Jun. 19, 2002.

BACKGROUND OF THE INVENTION

The present invention relates to the use of selective imidazoline receptor agonists and their physiologically compatible acid addition salts for the treatment and/or inhibition of functional disorders and/or diseases in larger mammals or humans which require inhibition or reduction of the activity of proteins which regulate the intracellular pH value and belong to the superfamily of bicarbonate transporters, and to the preparation of medicaments suitable for this treatment and/or inhibition.

SUMMARY OF THE INVENTION

It is an object of the invention to provide a method suitable for the treatment of functional disorders and/or diseases which require inhibition or reduction of the activity of proteins which regulate the intracellular pH value and which belong to the superfamily of bicarbonate transporters.

A further object of the invention is to provide a method for the treatment and/or inhibition of diseases which are selected from the group consisting of clinical conditions of bones which are caused by an undesirable amount of bone resorption, in particular osteoporosis, diseases of the gastrointestinal tract, in particular gastric ulcers, and neuronal and/or neuropsychiatric diseases connected with a pathologically altered (especially an increased) neuronal activity, in particular depression, Alzheimer's disease, eating disorders and schizophrenia.

According to the invention, selective imidazoline receptor agonists and their physiologically compatible acid addition salts are used in pharmaceutical preparations for the treatment and/or inhibition of functional disorders and/or diseases which require inhibition or reduction of the activity of proteins which regulate the intracellular pH value and belong to the superfamily of bicarbonate transporters, preferably for the treatment and/or inhibition of diseases selected from the group consisting of clinical conditions of bones which are caused by an undesirable amount of bone resorption, in particular osteoporosis, diseases of the gastrointestinal tract, in particular gastric ulcers, and neuronal and/or neuropsychiatric illnesses connected with a pathologically altered, preferably increased, neuronal activity, in particular depression, Alzheimer's disease, eating disorders and schizophrenia.

Suitable physiologically compatible acid addition salts of the selective imidazoline receptor agonists include salts with inorganic acids, for example hydrohalic acids, or with organic acids, for example lower aliphatic mono- or dicarboxylic acids such as acetic acid, fumaric acid or tartaric acid or aromatic carboxylic acids such as salicylic acid.

Compounds which represent selective imidazoline receptor agonists are already known, for example from U.S. Pat. No. 5,686,477 (=EP 710,658); U.S. Pat. No. 5,925,665 (=EP 846,688); PCT application no. WO 01/41764 and PCT application no. WO 00/02878, without thereby restricting the group of selective imidazoline receptor agonists. The 5-(aryloxymethyl)-oxazoline derivatives described in U.S. Pat. No. 5,686,477 are distinguished by a selective affinity for the Type 1 imidazoline receptor. Imidazoline derivatives are described in U.S. Pat. No. 5,925,665 which possess an affinity for binding to imidazoline receptors, but have hardly any affinity to the adrenergic receptors. PCT application WO 01/41764 describes isoquinoline and quinoline derivatives which possess an affinity for imidazoline receptors. PCT application WO 00/02878 discloses β-carboline derivatives as potential ligands for imidazoline receptors. The aforementioned compounds may be prepared in known manner in accordance with the processes described in the aforementioned patent publications or analogously to these processes.

From the above patent applications, mention should be made in particular of the following compounds, which represent selective imidazoline receptor agonists. First of all, mention should be made of the compound 5-[(2-bromophenoxy)methyl]-4,5-dihydro-oxazol-2-ylamine (S-23515) of Formula I which belongs to the 5-(aryloxymethyl)-oxazoline derivatives described in U.S. Pat. No. 5,686,477.

Furthermore, mention should be made of the compound 1-(4,5-dihydro-1H-imidazol-2-yl)-isoquinoline (BU98008) of Formula II which belongs to the isoquinoline and quinoline derivatives described in PCT application WO 01/41764. The aforementioned compounds may be prepared in known manner in accordance with the processes described in the aforementioned patent publications or analogously to these processes.

Furthermore, in particular the 5-[(2-imidazolin-2-yl)-amino]-pyrimidine derivatives described in U.S. Pat. No. 4,323,570 (=DE 2,849,537), which possess hypotensive properties, fall within the group of selective imidazoline receptor agonists. Of these, mention should be made, in particular, of the compound 4-chloro-5-[(4,5-dihydro-1H- imidazol-2-yl)-amino]-6-methoxy-2-methylpyrimidine (=moxonidine) of Formula III

Moxonidine-containing pharmaceutical preparations are commercially available as antihypertensives under the trade name Physiotens® and used medicinally as antihypertensives. It is known from the prior art that moxonidine is a selective ligand of the Type I imidazoline receptor (see also e.g. [Ernsberger (2000) Pharmacology of moxonidine: an I1-imidazoline receptor agonist. *J. Cardiovasc. Pharmacol.* 35: pp. 27-41]). The above compounds can be prepared in known manner according to the processes described in the aforementioned patent application or analogously to these processes.

Furthermore, the cyclopropylmethylamines described in U.S. Pat. No. 3,988,464 (=DE 2,362,754), which possess hypotensive properties, belong to the group of selective imidazoline receptor agonists. Of these, mention should be made in particular of the compound N-(dicyclopropylmethyl)-4,5-dihydro-2-oxazolamine(rilmenidine) of Formula IV

That rilmenidine is a selective imidazoline receptor agonist is already known from the prior art (see e.g. [Bock et al. (1999) Analysis of the receptor involved in the central hypotensive effect of rilmenidine and moxonidine. *Naunyn Schmiedebergs Arch. Pharmacol.* 359: 262-71]). The above compounds can be prepared in known manner according to the processes described in the aforementioned patent publication or analogously to these processes.

Furthermore, the aminopyrroline derivatives described in U.S. Pat. No. 6,300,366 (=EP 1,101,756), which are suitable for the treatment of cardiovascular diseases, inter alia hypertension, belong to the group of selective imidazoline receptor agonists. Of these, mention should be made in particular of the compound cis-/trans-dicyclopropylmethyl-(4,5-dimethyl-4,5-dihydro-3H-pyrrol-2-yl)-amine (LNP-509) of Formula V LNP-509 is a ligand which selects for the Type I1 imidazoline receptor and possesses hypotensive properties [Schann et al. (2001) Synthesis and biological evaluation of pyrrolinic isosteres of rilmenidine. Discovery of cis-/trans-dicyclopropylmethyl-(4,5-dimethyl-4,5-dihydro-3H-pyrrol-2-yl)-amine (LNP 509), an I1 imidazoline receptor selective ligand with hypotensive activity. *J. Med. Chem.* 44): 1588-93]. The above compounds can be prepared in known manner according to the processes described in the aforementioned patent application or analogously to these processes.

Also the substituted piperazine derivatives described in U.S. Pat. No. 5,492,912 (=EP 638,568), which are suitable for the treatment of non-insulin-dependent diabetes, belong to the group of selective imidazoline receptor agonists. Of these, mention should be made in particular of the compound 1-(2,4-dichlorobenzyl)-2-(4,5-dihydro-1H-imidazol-2-yl)-4-methylpiperazine (PMS-812, also referred to as S-21663) of Formula VI or the compound 1-methyl-4-(2,4-dichlorobenzyl)-2-(4,5-dihydro-1H-imidazol-2-yl)-piperazine, and also the compound 1,2-diisopropyl-2-(4,5-dihydro-1H-imidazol-2-yl)-piperazine (PMS-847, also referred to as S-22068) of Formula VII PMS-812 (S-21663) and PMS-847 (S-22068) are imidazoline derivatives which bind to imidazoline receptors [Rondu et al. (1997) Design and synthesis of imidazoline derivatives active on glucose homeostasis in a rat model of type II diabetes. 1. Synthesis and biological activities of N-benzyl-N'-(arylalkyl)-2-(4',5'-dihydro-1'H-imidazol-2'-yl)piperazines. *J. Med. Chem.* 40: 3793-803; Le Bihan et al. (1999) Design and synthesis of imidazoline derivatives active on glucose homeostasis in a rat model of type II diabetes. 2. Syntheses and biological activities of 1,4-dialkyl-, 1,4-dibenzyl-, and 1-benzyl-4-alkyl-2-(4',5'-dihydro-1'H-imidazol-2'-yl)piperazines and isosteric analogues of imidazoline. *J. Med. Chem.* 42: 1587-603]. The foregoing compounds can be prepared in known manner according to the processes described in the aforementioned patent application or analogously to these processes.

Living cells are equipped with mechanisms to maintain the intracellular pH value. First, cells are exposed to acidity resulting from their metabolism, and second, the electric potential difference at the cell membrane represents a considerable driving force on the influx of $H^+$-ions into the cells. In particular, two mechanisms are responsible for keeping the intracellular pH value constant, metabolic buffering and transport of acids and bases through the cell membrane. Of particular interest here are those proteins which transport protons and bicarbonate ions across the cell membrane.

The protein superfamily of the bicarbonate transporters comprises both the $Na^+$-independent chloride-bicarbonate exchangers (abbreviated to AE, for "anion exchange"), various $Na^+$/bicarbonate cotransporters (abbreviated to NBC) and also $Na^+$-dependent anion exchangers (abbreviated to NDAE), such as the $Na^+$-dependent chloride-bicarbonate exchanger (abbreviated to N(D)CBE, from "$Na^+$-driven chloride/bicarbonate exchanger"). One characteristic of most bicarbonate transporters is that they are inhibited relatively effectively by the compound 4,4'-diisothiocyanostilbene-4,4'-disulfonate (DIDS) [Boron (2001) Sodium-coupled bicarbonate transporters. JOP 24 (Suppl.): 176-81].

The $Na^+$-independent chloride-bicarbonate ($Cl^-/HCO_3^-$) exchanger AE catalyzes the release of the bicarbonate ion $HCO_3^-$ from the cell in exchange for including a chloride ion $Cl^-$ in the cell. This exchange is electrically neutral. This exchanger is known to play a part in particular in the regulation of the intracellular pH value, the cell volume and the intracellular chloride-ion concentration. This exchanger is generally activated by intracellular alkalosis. The gene family of the $Na^+$-independent chloride-bicarbonate ($Cl^-/HCO_3^-$) exchanger has hitherto comprised the three isoforms AE1, AE2 and AE3, which at the amino acid level particularly in the carboxy-terminal region possess high homology and differ in their expression patterns.

Thus for example in ventricular myocytes the AE proteins are activated by extracellular acidosis or intracellular alkalosis. As a reaction to a drop in the extracellular pH value, the AE proteins begin to export bicarbonate ions; consequently, a drop in the intracellular pH value occurs. If the pH value inside the cell is increased, the intracellular pH value is normalized again by the activity of the AE proteins. During an ischemia of the myocardium, inhibition of AE proteins in the ventricular myocytes is very useful, since the consequently reduced export of the intracellular bicarbonate ions prevents intracellular acidosis with its adverse consequences for the cells.

The Na+/bicarbonate cotransporters (NBC) catalyze the simultaneous transport of bicarbonate $HCO_3^-$ and $Na^+$ ions across the cell membrane. The transport may take place dependent on the expressed NBC isoform with a stoichiometry of 3:1, 2:1 or, electrically neutrally, of 1:1. Furthermore, transport may be in an outward direction (out of the cell) as in the kidney or an inward direction (into the cell) as in the heart, the pancreas or the brain.

The $Na^+$-dependent anion exchangers (NDAE or N(D) CBE) catalyze the simultaneous transport of bicarbonate $HCO_3^-$ and $Na^+$ ions across the cell membrane into the cell in exchange for releasing a chloride ion $Cl^-$ from the cell. The NBCEs seem to be of greatest importance for pH regulation in neurons. The activity of the NDAEs can in contrast be detected in neurons, in the kidney and in fibroblasts [Romero et al. (2000) Cloning and characterization of a Na+-driven anion exchanger (NDAE1). A new bicarbonate transporter. *J. Biol. Chem.* 275: 24552-9].

It has now surprisingly been found that selective imidazoline receptor agonists and their physiologically compatible acid addition salts possess very advantageous pharmacological properties. In particular, it has been shown that selective imidazoline receptor agonists are inhibitors of the proteins which regulate the intracellular pH value and belong to the superfamily of bicarbonate transporters and have an inhibiting action similar to that of the compound 4,4'-diisothiocyanostilbene-4,4'-disulfonate (DIDS), a standard inhibitor of bicarbonate transporter proteins. It follows from this that selective imidazoline receptor agonists and their physiologically compatible acid addition salts not only, as indicated in the patent applications cited above, bind selectively to imidazoline receptors and are suitable for the treatment of pathological conditions associated with imidazoline receptors, such as for example cardiovascular diseases, in particular hypertension, or non-insulin-dependent diabetes, but also can be used for the treatment and/or inhibition of functional disorders and/or diseases in larger mammals or humans which require inhibition or reduction of the activity of proteins which regulate the intracellular pH value and belong to the superfamily of bicarbonate transporters.

The functional disorders or diseases which can be treated by the compounds used according to the invention include in particular pathological conditions, the treatment of which requires inhibition or reduction of the activity of $Na^+$-independent chloride-bicarbonate ($Cl^-/HCO_3^-$) exchanger proteins (AE). Furthermore, the functional disorders or diseases which can be treated by the compounds used according to the invention include in particular pathological conditions, the treatment of which requires inhibition or reduction of the activity of $Na^+$-/bicarbonate ($Na^+/HCO_3^-$) cotransporter proteins (NBC). Furthermore, the functional disorders or diseases which can be treated by the compounds used according to the invention include in particular pathological conditions, the treatment of which requires inhibition or reduction of the activity of $Na^+$-dependent chloride/bicarbonate ($Cl^-/HCO_3^-$) exchanger proteins (NDAE and N(D)CBE).

Pharmacological evaluation of the compounds used according to the invention, which represent selective imidazoline receptor agonists, demonstrated in particular that selective imidazoline receptor agonists are suitable in pharmaceutical preparations for the treatment and/or inhibition of functional disorders or clinical conditions of bones which are caused by an undesirable amount of bone resorption.

Figure 1:
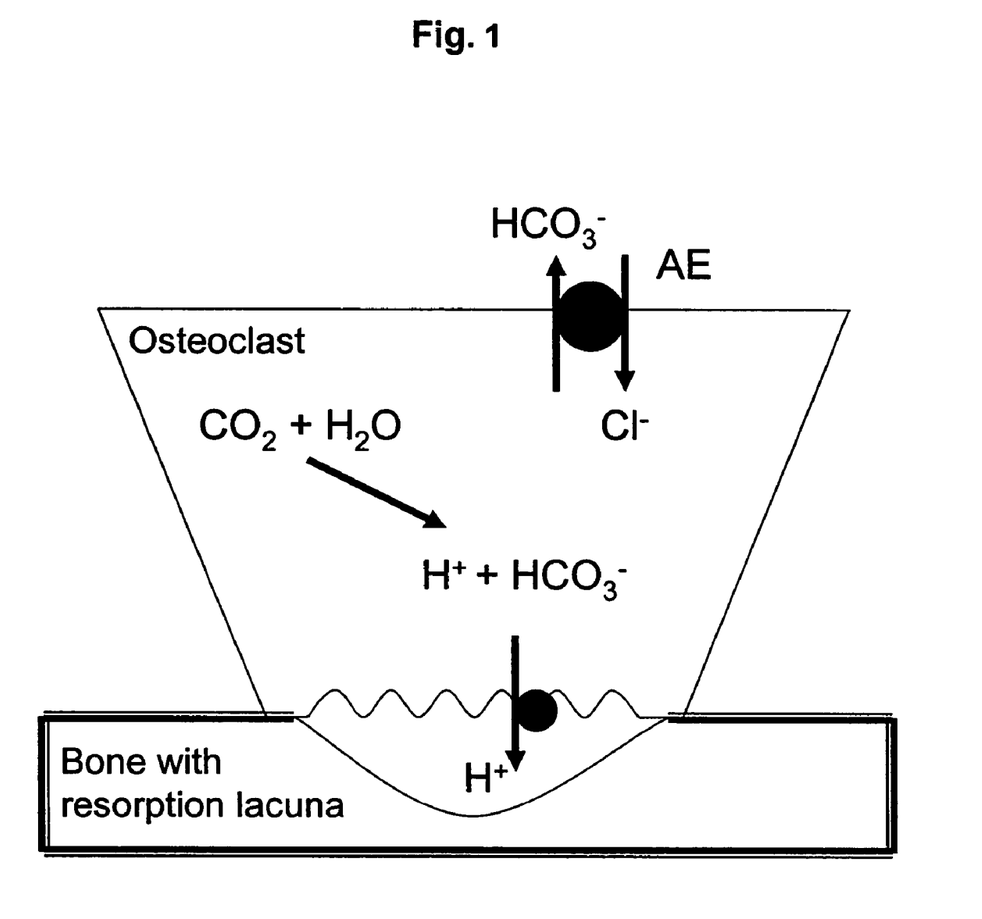

Human bones are subject to a continual dynamic remodelling process which involves bone resorption and bone build-up. These processes are controlled by specialized cell types: bone build-up is based on the deposition of bone matrix by osteoblasts, whereas bone resorption is based on the breakdown of bone matrix by osteoclasts. The majority of osteopathies are based on a disturbed equilibrium between bone formation and bone resorption. Thus the disease osteoporosis is characterized by a loss of bone matrix. Osteoclasts, the cells which are the most important participants in the bone resorption process, are polarized cells with a specialized region on the side facing the bone surface, what is called the "ruffled border" in English, see FIG. 1. Between the "ruffled border" and the bone surface is the resorption lacuna. The osteoclasts transport protons through a vacuole-type $H^+$-ATPase across the "ruffled border" into the resorption lacuna, so that the liquid located therein is acidified. The acidic surroundings, also in combination with proteolytic enzymes additionally secreted into the resorption lacuna, causes the bone material to be dissolved and hence the bone to be broken down. In the osteoclast itself, the protons are provided by hydration of $CO_2$ and subsequent dissociation into protons and bicarbonate ions. The constant transport of protons out of the cell results in intracellular alkalization, accompanied by an intracellular excess of bicarbonate ions. The bicarbonate ions are discharged via the AE protein located on the other side of the osteoclast by the simultaneous uptake of chloride ions. The electroneutrality is preserved by the transport of the Cl– ions on the bone side which takes place parallel to the proton transport. A reduction in the activity of the AE protein has been proved to reduce the process of bone resorption [Teti et al. (1989) Cytoplasmic pH regulation and chloride/bicarbonate exchange in avian osteoclasts. J. Clin. Invest. 83: 227-33; Hall et al. (1989) Optimal bone resorption by isolated rat osteoclasts requires chloride/bicarbonate exchange. Calcif. Tissue Int. 45: 378-80].

Accordingly, the selective imidazoline receptor agonists used according to the invention, since they reduce or inhibit bone resorption by the osteoclasts by the reduction in the activity of the AE protein of the osteoclasts, are suitable in particular in pharmaceutical preparations for the treatment and/or inhibition of functional disorders or clinical conditions of bones which are caused by an undesirable amount of bone resorption. Osteopathies against which selective imidazoline receptor agonists can preferentially be used are in particular osteoporosis, hypercalcaemia, osteopenia, for example caused by metastases, dental diseases, hyperparathyroidism, periarticular erosions in rheumatoid arthritis and Paget's disease. Furthermore, the selective imidazoline receptor antagonists used according to the invention may be used for alleviating, avoiding or therapy of osteopathies caused by glucocorticoid, steroid or corticosteroid therapy or by a deficiency of sex hormones. All these diseases are characterized by loss of bone substance based on the imbalance between bone build-up and bone breakdown.

Pharmacological evaluation of the compounds used according to the invention, which represent selective imidazoline receptor agonists, demonstrated in particular that selective imidazoline receptor agonists are suitable in pharmaceutical preparations for the treatment and/or inhibition of functional disorders or diseases of the gastrointestinal tract, e.g. gastric ulcers, duodenal ulcers, hypersecretion of gastric acid and motion sickness.

In fact, the parietal cells of the stomach possess a basolateral AE (isoform AE2), the activity of which is essential for maintaining secretion of gastric acid by apical $H^+/K^+$ ATPase [Muallem et al. (1988) Activation of the Na+/H+ and Cl–/HCO3– exchange by stimulation of acid secretion in the parietal cell. J. Biol. Chem. 263: 14703-11]. Inhibiting this AE protein results in reduced secretion of gastric acid. The epithelial cells of the large intestine possess an apical AE protein which is involved in the secretion of water and bicarbonate and represents the binding site of the cholera toxin.

Pharmacological evaluation of the compounds used according to the invention, which represent selective imidazoline receptor agonists, demonstrated in particular that selective imidazoline receptor agonists are suitable in pharmaceutical preparations for the treatment and/or inhibition of neuronal and neuropsychiatric diseases connected with a pathologically changed, preferably increased, neuronal activity, such as for example depression, Alzheimer's disease, eating disorders (anorexia), schizophrenia, agitation (motor and affective restlessness), anxiety, sleep disturbance, epilepsy, and general illnesses based on altered dopamine release, illnesses resulting from ischemic/hypoxic events and age-related degenerative illnesses.

Increased neuronal activity results in long-lasting intracellular acidification (increase in proton concentration), which makes the cell refractory to a new neuronal impulse. In this regard, intracellular protons function similarly to neuromodulatory factors, comparably with other types of intracellular messengers ("second messengers") [Takahashi & Copenhagen (1996) Modulation of neuronal function by intracellular pH. Neurosci. Res. 24: 109-16; Trapp et al. (1996) Acidosis of rat dorsal vagal neurons in situ during spontaneous and evoked activity. J. Physiol. 496: 695-710]. To overcome these refractory conditions, the intracellular acidification must be neutralized again, i.e. the lowered intracellular pH value must be raised to a physiologically neutral pH value. Anion exchanger proteins such as NDAE and N(D)CBE are responsible for this neutralization, and also the presence of extracellular bicarbonate ions is essential for this [Canzoniero et al. (1996) Recovery from NMDA-induced intracellular acidification is delayed and dependent on extracellular bicarbonate. Am. J. Physiol. 270: C593-9]. Inhibition of these exchangers results in the neutralization of the intracellular pH value being slowed down, i.e. the intracellular proton concentration remains elevated for longer; as a consequence, the cells are refractory for longer against a new neuronal impulse [Bonnet et al. (2000) Alteration of intracellular pH and activity of CA3-pyramidal cells in guinea pig hippocampal slices by inhibition of transmembrane acid extrusion. Brain Res. 872: 116-24].

Where the invention relates to the treatment of disorders of the central nervous system which are associated with an altered intracellular pH value, the corresponding illnesses are preferably Alzheimer's disease, illnesses caused by the altered release of dopamine or other transmitters or illnesses due to ischemic-hypoxic events.

In Alzheimer's disease, the increased proliferation of Alzheimer lymphoblasts is accompanied by intracellular alkalization, which can be influenced by inhibiting of anion exchangers, e.g. those similar to the Na+/H+ exchanger [Urcelay E., Ibarreta D., Parrilla R., Ayuso M. S., Martin-Requero A. Enhanced proliferation of lymphoblasts from patients with Alzheimer dementia associated with calmodulin-dependent activation of the Na+/H+ exchanger; Neurobiol. Dis. 2001; 8: 289-98]. Furthermore, it has been reported that changes in the structure of anion exchangers on ageing and particularly in Alzheimer's disease can be influenced by an inhibitor of the anion exchanger [Bosman G. J., Renkawek K., Van Workum F. P., Bartholomeus I. G., Marini S., De Grip W. J. Neuronal anion exchange proteins in Alzheimer's disease pathology. J. Neural. Transm. Suppl. 1998; 54: 248-57].

With regard to illnesses based on altered dopamine release, it should be noted that the neuronal dopamine release is modulated by the intracellular pH value. The connections between the intracellular acidification and the increased dopamine release are discussed by Pothos [Regulation of dopamine quantal size in midbrain and hippocampal neurons. Behav. Brain. Res. 2002; 130: 203-7]. The inhibition of anion transporters which counteract acidification can therefore influence the dopamine release.

Illnesses resulting from ischemic-hypoxic events are connected with the intracellular pH value as follows: since rapid re-establishment of the acidic intracellular pH value in conjunction with ischemic-hypoxic events with the exchange of H+ for Na+ by the Na+/H+ exchanger is associated with subsequent Ca2+ accumulation via the Na+/Ca2+ exchanger, the risk of cell damage is increased. The inhibition of anion transporters participating in the extracellular Na+ influx therefore exhibits a protective action. This accords with the increasing observation that inhibitors of the Na+/H+ exchanger have various protective effects after ischemic-hypoxic events [Avkiran M., Marber M. S. Na(+)/

H(+) exchange inhibitors for cardioprotective therapy: progress, problems and prospects. J. Am. Coll. Cardiol. 2002 Mar. 6; 39(5): 747-53].

The invention comprises the use of selective imidazoline receptor agonists in pharmaceutical preparations for the treatment and inhibition of clinical conditions of bones which are caused by an undesirable amount of bone resorption, of diseases of the gastrointestinal tract, in particular gastric ulcers, of neuronal and neuropsychiatric diseases connected with a pathologically altered, preferably increased, neuronal activity, in particular depression, Alzheimer's disease, eating disorders and schizophrenia, and furthermore of diseases based on a disturbance in the acid-base balance (acidosis and alkalosis) or in the hydroelectrolytic balance. In particular, the invention comprises the use of selective imidazoline receptor agonists in pharmaceutical preparations for the treatment and inhibition of osteoporosis.

Furthermore, the invention comprises in particular the use of a compound selected from the group consisting of moxonidine, rilmenidine, LNP-509, S-23515, PMS-812, PMS-847 and BU-98008 or their physiologically compatible acid addition salts in pharmaceutical preparations for the treatment and/or inhibition of functional disorders and/or diseases in larger mammals or humans which require inhibition or reduction of the activity of proteins which regulate the intracellular pH value and which belong to the superfamily of bicarbonate transporters. In particular, the invention comprises the use of one of the above compounds or their physiologically compatible acid addition salts in pharmaceutical preparations for the treatment and/or inhibition of functional disorders or diseases in larger mammals or humans which require inhibition or reduction of the activity of $Na^+$-independent chloride-bicarbonate ($Cl^-/HCO_3^-$) exchanger (AE) proteins, of $Na^+$/bicarbonate ($Na^+/HCO_3^-$) cotransporter (NBC) proteins or/and of $Na^+$-dependent chloride-bicarbonate ($Cl^-/HCO_3^-$) exchanger (NDAE and N(D)CBE) proteins.

In particular, the invention comprises the use of a compound selected from the group consisting of moxonidine, rilmenidine, LNP-509, S-23515, PMS-812, PMS-847 and BU-98008 or their physiologically compatible acid addition salts in pharmaceutical preparations for the treatment and/or inhibition of clinical conditions of bones which are caused by an undesirable amount of bone resorption, in particular osteoporosis, of diseases of the gastrointestinal tract, in particular gastric ulcers, or of neuronal and/or neuropsychiatric illnesses connected with a pathologically altered, preferably increased, neuronal activity, in particular depression, Alzheimer's disease, eating disorders and schizophrenia, in larger mammals or humans. Furthermore, the invention comprises in particular the use of one of the above compounds or their physiologically compatible acid addition salts in pharmaceutical preparations for the treatment and/or inhibition of osteoporosis in larger mammals or humans.

Furthermore, the invention comprises the use of all the aforementioned compounds, in particular a compound selected from the group consisting of moxonidine, rilmenidine, LNP-509, S-23515, PMS-812, PMS-847 and BU-98008, or their physiologically compatible acid addition salts in pharmaceutical preparations for the treatment and/or inhibition of one of the aforementioned functional disorders and/or diseases, in particular osteoporosis, in peri- or postmenopausal women.

It has now been found that moxonidine has an inhibitory effect on the proteins which regulate the intracellular pH value and belong to the superfamily of bicarbonate transporters. In particular, it has been discovered that moxonidine is a selective inhibitor of the $Na^+$-independent chloride-bicarbonate exchanger (AE) proteins. The intracellular pH value is influenced by the reduction of the exchange or transport of bicarbonate ions across the cell membrane. The inhibitory action of moxonidine on bicarbonate transporter proteins is comparable to the action of 4,4'-diisothiocyanostilbene-4,4'-disulfonate (DIDS), a compound having an entirely different chemical structure. Due to their inhibitory action on bicarbonate transporter proteins, moxonidine and its pharmacologically acceptable acid addition salts are therefore suitable in particular in pharmaceutical preparations for the treatment and/or inhibition of functional disorders and/or diseases in larger mammals or humans which require inhibition or reduction of the activity of proteins which regulate the intracellular pH value and which belong to the superfamily of bicarbonate transporters.

In particular, the invention comprises the use of moxonidine or its physiologically compatible acid addition salts in pharmaceutical preparations for the treatment and/or inhibition of functional disorders or diseases which require inhibition or reduction of the activity of $Na^+$-independent chloride-bicarbonate ($Cl^-/HCO_3^-$) exchanger (AE) proteins, of $Na^+$/bicarbonate ($Na^+/HCO_3^-$) cotransporter (NBC) proteins or/and of $Na^+$-dependent chloride-bicarbonate ($Cl^-/HCO_3^-$) exchanger (NDAE and N(D)CBE) proteins, especially for the treatment and/or inhibition of functional disorders or diseases in larger mammals and humans which are connected with clinical conditions of bones which are caused by an undesirable amount of bone resorption, with diseases of the gastrointestinal tract, or with neuronal and/or neuropsychiatric illnesses connected with a pathologically altered, preferably increased, neuronal activity. In particular, the invention comprises in particular the use of moxonidine or its physiologically compatible acid addition salts in pharmaceutical preparations for the treatment and/or inhibition of osteoporosis in larger mammals or humans. Furthermore, the invention comprises the use of moxonidine or its physiologically compatible acid addition salts in pharmaceutical preparations for the treatment and/or inhibition of one of the aforementioned functional disorders and/or diseases, in particular osteoporosis, in peri- or postmenopausal women.

In a further aspect, the invention comprises the use of moxonidine or its physiologically compatible acid addition salts in pharmaceutical preparations for the simultaneous treatment and/or inhibition of osteoporosis and of hypertension in larger mammals or humans, in particular in peri- or postmenopausal women.

For the treatment according to the invention of functional disorders and/or diseases which require inhibition or reduction of the activity of proteins which regulate the intracellular pH value and belong to the superfamily of bicarbonate transporters, in particular of $Na^+$-independent chloride-bicarbonate ($Cl^-/HCO_3^-$) exchanger (AE) proteins, of $Na^+$/bicarbonate ($Na^+/HCO_3^-$) cotransporter (NBC) proteins or/and of $Na^+$-independent chloride-bicarbonate ($Cl^-/HCO_3^-$) exchanger (NDAE and N(D)CBE) proteins, in particular for the treatment and/or inhibition of clinical conditions of bones which are caused by an undesirable amount of bone resorption, in particular osteoporosis, of diseases of the gastrointestinal tract, in particular gastric ulcers, or of neuronal and/or neuropsychiatric illnesses connected with a pathologically altered, preferably increased, neuronal activity, in particular depression, Alzheimer's disease, eating disorders and schizophrenia, selective imidazoline receptor agonists, in particular compounds selected from the group consisting of moxonidine, rilmenidine, LNP-509, S-23515, PMS-812, PMS-847 and BU-98008, and very particularly moxonidine, and their physiologically compatible acid addition salts may be administered in conventional pharmaceutical preparations orally, intravenously or alternatively transdermally.

Thus, selective imidazoline receptor agonists, in particular compounds selected from the group consisting of moxonidine, rilmenidine, LNP-509, S-23515, PMS-812, PMS-847 and BU-98008, and very particularly moxonidine, and their physiologically compatible acid addition salts may be contained, together with conventional pharmaceutical auxiliaries and/or excipients, in solid or liquid pharmaceutical preparations in an amount which is effective for the treatment of functional disorders and/or diseases which require inhibition or reduction of the activity of proteins which regulate the intracellular pH value and belong to the superfamily of bicarbonate transporters, in particular of $Na^+$-independent chloride-bicarbonate ($Cl^-/HCO_3^-$) exchanger (AE) proteins, of $Na^+$/bicarbonate ($Na^+/HCO_3^-$) cotransporter (NBC) proteins or/and of $Na^+$-dependent chloride-bicarbonate ($Cl^-/HCO_3^-$) exchanger (NDAE and N(D)CBE) proteins, in particular for the treatment and/or inhibition of clinical conditions of bones which are caused by an undesirable amount of bone resorption, in particular osteoporosis, of diseases of the gastrointestinal tract, in particular gastric ulcers, or of neuronal and/or neuropsychiatric diseases connected with a pathologically altered, preferably increased, neuronal activity, in particular depression, Alzheimer's disease, eating disorders and schizophrenia. Examples of solid preparations which can be formulated for direct or delayed active-substance release include preparations which can be administered orally, such as tablets, coated tablets, capsules, powders or granules, or alternatively suppositories and patches (transdermal therapeutic systems). These solid preparations may contain conventional pharmaceutical inorganic and/or organic excipients such as lactose, talcum or starch, in addition to conventional pharmaceutical auxiliaries, for example lubricants or tablet disintegrating agents. In the case of patches, the active substance is stored in an active-substance reservoir, in particular e.g. an active-substance matrix (e.g. a polymer matrix). Liquid preparations such as solutions, suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or excipients in known manner. To prepare solid medicament forms, the active substances may, for example, be mixed with the auxiliaries and/or excipients in conventional manner and may be wet or dry granulated. The granules or powder may be filled directly into capsules or be pressed into tablet cores in a conventional manner. These may be coated in known manner, if desired. Patches or transdermal therapeutic systems may be constructed in a conventional manner, e.g. from cover film, active-substance reservoir (self-adhesive or with additional adhesive layer) and backing film both as matrix-controlled and as membrane-controlled (i.e. equipped with an additional control membrane) systems.

BRIEF DESCRIPTION OF THE DRAWING

The invention will be described in further detail hereinafter with reference to the accompanying Drawing FIG. 1, which is a schematic representation of an osteoclast. The drawing shows a schematic representation of an osteoclast with its "ruffled border". Between the "ruffled border" and the bone surface is the resorption lacuna, into which protons ($H^+$) are secreted. In the cell, hydrated $CO_2$ dissociates into protons ($H^+$) and bicarbonate ions ($HCO_3^-$). The bicarbonate ions are transported out of the osteoclast by the $Na^+$-independent chloride-bicarbonate ($Cl^-/HCO_3^-$) exchangers (AE). In return, chloride ions ($Cl^-$) pass into the cell.

PHARMACOLOGICAL TESTS

The pharmacological effects of selective imidazoline receptor agonists and their pharmacologically acceptable acid addition salts are demonstrated in pharmacological standard tests using the example of the selective imidazoline receptor agonist moxonidine.

Measurement of Bicarbonate Transporter Protein Activity in Adult Cardiac Fibroblasts The investigations were carried out on cardiac fibroblasts isolated from the left ventricle of the myocardium of 6-week-old Wistar rats. Myocardial tissue was placed in HBSS medium without $Ca^{2+}$ and $Mg^{2+}$ (GibcoBRL), cut into small pieces which were incubated with 1 mg/ml collagenase A (Roche) with continuous shaking for 10 minutes in HBSS medium. The first supernatant was discarded and the incubation operation was repeated three times, the supernatant being collected each time in a tube with 5 ml HBSS medium. After centrifuging at 160×g for 10 min, the pellet was re-suspended in a flask with DMEM (GibcoBRL), to which 10% foetal calf serum (FCS, from Sigma) was added. After 1 hour, all those cells which did not stick to the flask wall were separated out. The flasks were incubated in an air-humidified incubator with 5% $CO_2$ and at 37° C. Cardiac fibroblasts, which grew in a typical monolayer, were cultivated by standard cell culture techniques and at subconfluence were transferred into new flasks in a 1:3 ratio [Brilla et al. (1994) Collagen metabolism in cultured adult rat cardiac fibroblasts: response to agiotensin II and aldosterone. *J. Mol. Cell Cardiol.* 26: 809-820]. Immunohistochemical characterization ruled out the possibility that the isolated cells were endothelial cells or vascular cells of the smooth musculature; rather, they were fibroblasts.

The intracellular pH value of an individual cell was measured using the fluorescent marker BCECF (2',7'-bis-(2-carboxymethyl)-5-[and -6]-carboxyfluorescein from Molecular Probes), the fluorescent intensity of which is pH-dependent. The cardiac fibroblasts were grown on glass microscope slides until at subconfluence, and were then laden with BCECF-acetoxymethyl ester. The fibroblasts thus pre-treated were washed with PBS and then preincubated with various test solutions and then rinsed. In so doing, the intracellular fluorescence of the BCECF was measured using an inverted microscope, to which a "PTI 710 Photon Counting Detection" system (Photon Technology International) with two monochromators was connected. The data were analysed using a fluorescence spectrometer. The measurement results—fluorescence signals—were converted into pH values using a calibration curve.

Composition of the bicarbonate solution: 118 mmole/liter NaCl, 4.7 mmole/liter KCl, 2.5 mmole/liter CaCl2×2 H2O, 1.6 mmole/liter MgCl2×7 H2O, 24.9 mmole/liter NaHCO3, 1.2 mmole/liter KH2PO4, 5.6 mmole/liter glucose and either 0.4% or 10% FCS, equilibrated with 20% O2 and 5% $CO_2$ for at least 30 minutes to ensure a pH value of 7.4.

The individual test solutions were based on the above bicarbonate solution and contained the following concentration of the compounds below:

$10^{-6}$ mole/liter guanabenz (Sigma)
$10^{-6}$ mole/liter to $10^{-9}$ mole/liter moxonidine
$10^{-3}$ mole/liter $H_2$-DIDS (Molecular Probes)

Intracellular alkalization of the cells was achieved by rinsing with a 5 mmole/liter $NH_4Cl$-containing bicarbonate solution ($NH_4Cl$ pulse). Subsequent washing-out of the $NH_4Cl$ by rinsing the cells with fresh bicarbonate solution results in intracellular acidification.

The measurement of the change in pH value following alkalization shows the activity of the $Na^+$-independent chloride-bicarbonate ($Cl^-/HCO_3^-$) exchanger (AE) protein, whereas the measurement of the change in pH value following acidification provides information about the activity of the $Na^+$/bicarbonate ($Na^+/HCO_3^-$) cotransporter (NBC) protein or/and of the $Na^+$-dependent chloride-bicarbonate ($Cl^-/HCO_3^-$) exchanger (NDAE and N(D)CBE) protein.

The effect of moxonidine, DIDS and guanabenz on the change in the intracellular pH value after alkalization of the cells is determined by an $NH_4Cl$ pulse. To this end, the BCECF-laden cardiac fibroblasts were preincubated for 30 minutes with a bicarbonate test solution containing one of the above compounds. Then the response of the intracellular pH value of the cells thus pre-treated to a 5 mmole/liter $NH_4Cl$ pulse was measured over time. Also the change in pH value which took place during the subsequent washing-out of the $NH_4Cl$ (intracellular acidification) was further measured over time. The cells pre-treated with moxonidine or DIDS, compared with the cells pre-treated with guanabenz or the non-pre-treated cells (control), exhibited a considerably longer recovery after the intracellular alkalization. To quantify the inhibitory effects, the percentage of the change in pH value still present relative to the maximum alkaline or maximum acidic pH value achieved was calculated. The proportion of the change in pH value still present after returning from the alkaline was determined 5 minutes and 8 minutes after the maximum alkaline pH value was achieved, whereas the corresponding value after recovery from the acidic was determined 1 minute after the maximum acidic pH value was achieved.

Table 1 shows the effect of $10^{-6}$ mole/liter moxonidine and $10^{-6}$ mole/liter guanabenz on the change in the alkali loading of cardiac fibroblasts after intracellular alkalization by an $NH_4Cl$ pulse. What is given is the percentage of the change in pH value still present, relative to the maximum alkaline pH value reached after 5 and 8 min. The values are the mean value and standard deviation from 3 to 5 experiments.

TABLE 1

|  | After 5 min | after 8 min |
|---|---|---|
| Control: | 24.9 ± 14.8% | 14.4 ± 10.8% |
| Moxonidine | 58.8 ± 12.0% | 41.9 ± 24.4% |
| Guanabenz | 20.6 ± 5.2% | 9.9 ± 2.7% |

The dose-effect curve for the inhibitory effect of moxonidine on the recovery from the alkaline pH showed that moxonidine even in a concentration of $10^{-8}$ mole/liter has a significantly inhibitory action.

Furthermore, the activity of the $Na^+$/bicarbonate ($Na^+/HCO_3^-$) cotransporter (NBC) protein or/and of the $Na^+$-dependent chloride-bicarbonate ($Cl^-/HCO_3^-$) exchanger (NDAE and N(D))CBE) protein can be determined from its activation due to intracellular acidification according to the ammonium method [Boron & De Weer (1976) Intracellular pH transients in squid giant axons caused by CO2, NH3, and metabolic inhibitors. *J. Gen. Physiol.* 67: 91-112].

Pharmacological Test Relating to the Effect of the Compounds in Pathological Changes to Bones The inhibiting action of the test substances on the resorption of bone material was tested on a cell culture of chicken osteoclasts. Both the proton secretion into the extracellular space and the activity of the AE protein were measured in the presence and in the absence of the test substances. The activity of the AE protein was determined by measuring the cytosolic pH value in reaction to the change in the ionic composition of the extracellular medium and in reaction to the addition of the test substances or of control substances with a known inhibiting or stimulating action [Teti et al. (1989) Cytoplasmic pH regulation and chloride/bicarbonate exchange in avian osteoclasts. *J. Clin. Invest.* 83: 227-33; Hall et al. (1989) Optimal bone resorption by isolated rat osteoclasts requires chloride/bicarbonate exchange. *Calcif. Tissue Int.* 45: 378-80].

The inhibiting action of the test substances on resorption of bone material was investigated in an in vitro test. Osteoclasts isolated from newborn rats were brought into direct contact with discs of bone material from calves and were incubated together for at least 6 hours in the presence and in the absence of the test substances. Following the incubation, each bone disc was investigated using a microscope in order to determine the extent of bone resorption [Chambers et al. (1985) The effect of calcium-regulating hormones and prostaglandins on bone resorption by osteoclasts disaggregated from neonatal rabbit bones. *Endocrinology* 116: 234-9].

Pharmacological Test Relating to the Effect of the Compounds on Gastrointestinal Ulcers The inhibiting effect of the test substances on the secretion of gastric acid was tested on a culture of parietal cells from rabbits. The activity of the AE protein and the associated acid secretion was measured in the presence and in the absence of the test substances both under basal conditions and after stimulation of acid production by the addition of known stimulating compounds [Muallem et al. (1988) Activation of the Na+/H+ and Cl–/HCO3– exchange by stimulation of acid secretion in the parietal cell. *J. Biol. Chem.* 263: 14703-11].

The inhibiting effect of the test substances on the occurrence of stress-induced gastrointestinal ulcers was tested on rats. In this model, rats were subjected to stress by immobilizing them and partly submerging them in warm water at 22° C. for 6 hours. The occurrence of gastric lesions and their severity was compared in control rats and rats treated 30 minutes before being subjected to stress with a preventive dose of the test substances [Takagi & Okabe (1968) The effects of drugs on the production and recovery processes of the stress ulcer. *Jpn. J. Pharmacol.* 18: 9-18].

Pharmacological Test Relating to the Effect of the Compounds in Neuronal or Neuropsychiatric Diseases Associated with Pathologically Altered, in Particular Increased, Neuronal Activity Increased neuronal activity results in long-lasting intracellular acidification (increase in proton concentration), which makes the cell refractory to a new neuronal impulse.

Bicarbonate transporter proteins are responsible for the intracellular neutralization which then follows. Inhibition of this exchanger results in slowing of the neutralization of the intracellular pH value, and consequently the cells are refractory for longer to a new neuronal impulse. The inhibiting action of the test substances on the neuronal bicarbonate transporter proteins was investigated on hippocampal tissue sections from guinea pigs, by measuring both the intracellular pH value and the electric membrane potential of CA3-pyramidal cells in the presence and in the absence of the test substances and in comparison with control substances with known inhibiting or stimulating action [Bonnet et al. (2000) Alteration of intracellular pH and activity of CA3-pyramidal cells in guinea pig hippocampal slices by inhibition of transmembrane acid extrusion. *Brain Res.* 872: 116-24].

The test substance moxonidine, which is a selective imidazoline receptor agonist, completely surprisingly achieved an inhibiting effect on proteins which regulate the intracellular pH value and which belong to the superfamily of bicarbonate transporters. In particular, it was discovered that moxonidine represents a selective inhibitor both of the $Na^+$-independent chloride-bicarbonate ($Cl^-/HCO_3^-$) exchanger (AE) proteins and of the $Na^+$/bicarbonate ($Na^+$/$HCO_3^-$) cotransporter (NBC) proteins or/and of the $Na^+$-dependent chloride-bicarbonate ($Cl^-/HCO_3^-$) exchanger (NDAE and N(D)CBE) proteins. The inhibitory action of moxonidine on bicarbonate transporter proteins is comparable to the action of 4,4'-diisothiocyanostilbene-4,4'-disulfonate (DIDS), a compound having an entirely different chemical structure, the inhibitory action of which on bicarbonate transporters is known from the prior art [Boron (2001) Sodium-coupled bicarbonate transporters. *JOP* 24 (Suppl.): 176-81]. That the observed action of moxonidine cannot be ascribed to its alpha-2 adrenergic properties is shown by the comparison with the compound guanabenz, a selective alpha-2 agonist established in the prior art [Hieble & Ruffolo (1995) Possible structural and functional relationships between imidazoline receptors and alpha 2-adrenoceptors. *Ann. N.Y. Acad. Sci.* 763:8-21].

The foregoing test results therefore show that moxonidine and related compounds, such as other selective imidazoline receptor agonists, and their pharmacologically acceptable acid addition salts are capable of reducing the activity of bicarbonate transporter proteins and are therefore suitable for the treatment and/or inhibition of functional disorders and/or diseases in larger mammals or humans which require inhibition or reduction of the activity of proteins which regulate the intracellular pH value and which belong to the superfamily of bicarbonate transporters. The named compounds can therefore be used advantageously in particular for the treatment and/or inhibition of diseases of the gastrointestinal tract, in particular gastric ulcers, of clinical conditions of bones which are caused by an undesirable amount of bone resorption, in particular osteoporosis, or of [neuronal and/or neuropsychiatric illnesses] connected with a pathologically altered, in particular increased, neuronal activity.

The doses to be used may vary individually and will naturally vary according to the type of selective imidazoline receptor agonist used, the condition to be treated and the form of administration. Generally, the daily doses for treating the above functional disorders and/or diseases, in particular osteoporosis, in humans for oral administration are in the range of 0.01 to 1000 mg, for example approximately 0.1 to 100 mg, preferably approximately 0.2 to 10 mg. The above selective imidazoline receptor agonists, in particular a compound selected from the group consisting of moxonidine, rilmenidine, LNP-509, S-23515, PMS-812, PMS-847 and BU-98008, and very particularly moxonidine, or their pharmacologically acceptable acid addition salts may be administered in pharmaceutical preparations both for immediate and for delayed, regulated and/or controlled active-substance release. It goes without saying for the person skilled in the art that preparations with delayed, regulated and/or controlled active-substance release may contain larger amounts of active substance than preparations for immediate active-substance release.

The following example is intended to explain the preparation of a pharmaceutical preparation containing moxonidine—selected by way of example of a selective imidazoline receptor agonist—or a pharmaceutically acceptable salt thereof in greater detail, but without limiting the scope of the invention.

| Example: Moxonidine-containing film-coated tablets Composition: | |
|---|---|
| Tablet cores: | |
| Moxonidine | 0.025 parts |
| Lactose | 9.575 parts |
| Povidone USP | 0.070 parts |
| Crospovidone USP | 0.300 parts |
| Magnesium stearate | 0.030 parts |
| (Water | 0.750 parts) |
| Total solids | 10.000 parts |
| Film coating: | |
| Hydroxypropylmethyl cellulose | 0.156 parts |
| 30%-strength aqueous ethylcellulose dispersion | 0.480 parts |
| (=solid) | (0.144) parts |
| Polyethylene glycol 6000 | 0.030 parts |
| Titanium dioxide | 0.150 parts |
| Talc | 0.1197 parts |
| Red iron oxide | 0.0003 parts |
| (Water | 3.864 parts) |
| Total solids | 0.600 parts |
| Total amount of film coating suspension | 4.800 parts |

4.8 kg of the above film coating suspension was used for coating 10,000 tablet cores each weighing 100 mg.

Production of Tablet Cores

The moxonidine and the lactose were mixed. The mixture was moistened thoroughly with a solution of the binder Povidone in water, thoroughly kneaded and the resulting product was spread on trays and dried at a temperature of approx. 50° C. to a moisture content of at most 0.5%. The dried product was passed through a 0.75 mm sieve (Frewitt machine). Once the resulting granules had been mixed with Crospovidone and magnesium stearate, tablet cores of a weight of 100 mg were pressed therefrom, so that each tablet core contained 0.25 mg active substance.

Preparation of the Film Coating Suspension

The hydroxypropylmethyl cellulose and the polyethylene glycol 6000 were dissolved in part of the water. A suspension of talc, titanium dioxide and iron oxide in the remaining water was added to this solution with stirring. The resulting suspension was diluted with gentle stirring with the 30%-strength aqueous ethylcellulose dispersion.

Film-Coating of the Tablet Cores

The film coating suspension was sprayed on to the tablet cores in a film-coating apparatus, while warm air at approximately 70° C. warmed the tablet cores to a temperature of approximately 45° C. Then the film-coated tablets were dried for 16 hours at a temperature of approximately 45° C.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating a clinical bone condition involving an undesirable amount of bone resorption selected from the group consisting of osteoporosis, hypercalcaemia, osteopenia, Paget's disease and osteopathies caused by glucocorticoid, steroid or corticosteroid therapy or by a sex hormone deficiency in a human or larger mammal in need thereof, said method comprising administering to said human or larger mammal a pharmaceutically effective amount of a selective imidazoline receptor agonist selected from the group consisting of moxonidine, rilmenidine, cis-/trans-dicyclopropylmethyl-(4,5-dimethyl-4,5-dihydro-3H-pyrrol-2-yl)-amine, 5-[(2-bromophenoxy)methyl]-4,5-dihydro-oxazol-2-ylamine, 1-(2,4-dichlorobenzyl)-2-(4,5-dihydro-1H-imidazol-2-yl)-4-methylpiperazine, 1,2-diisopropyl-2-(4,5-dihydro-1H-imidazol-2-yl)-piperazine, and 1-(4,5-dihydro-1H-imidazol-2-yl)-isoquinoline or a physiologically compatible salt thereof, whereby Na+-independent chloride-bicarbonate exchanger proteins are reduced.

2. A method according to claim 1, wherein the clinical bone condition is osteoporosis.

3. A method according to claim 1, wherein the selective imidazoline receptor agonist is moxonidine.

4. A method according to claim 1, wherein the human or larger mammal is a perimenopausal or postmenopausal female.

5. A method of simultaneously treating osteoporosis and hypertension in a human or larger mammal in need thereof, said method comprising administering to said human or larger mammal a pharmaceutically effective amount of moxonidine or a physiologically compatible salt thereof.

6. A method according to claim 5, wherein the human or larger mammal is a perimenopausal or postmenopausal female.

* * * * *